US012600980B2

(12) United States Patent
Mauny et al.

(10) Patent No.: US 12,600,980 B2
(45) Date of Patent: Apr. 14, 2026

(54) DISEASE RESISTANT MELON PLANTS

(71) Applicant: Syngenta Crop Protection AG, Basel (CH)

(72) Inventors: Adrien Mauny, Sarrians (FR); Marc Oliver, Saint-Sauveur (FR); Bruno Foncelle, Sarrians (FR)

(73) Assignee: SYNGENTA CROP PROTECTION AG, Basel (CH)

( * ) Notice: Subject to any disclaimer, the term of this patent is extended or adjusted under 35 U.S.C. 154(b) by 502 days.

(21) Appl. No.: 18/002,502

(22) PCT Filed: Jun. 25, 2021

(86) PCT No.: PCT/EP2021/067539
§ 371 (c)(1),
(2) Date: Dec. 20, 2022

(87) PCT Pub. No.: WO2022/002795
PCT Pub. Date: Jan. 6, 2022

(65) Prior Publication Data
US 2023/0227839 A1    Jul. 20, 2023

(30) Foreign Application Priority Data

Jun. 29, 2020    (EP) ..................................... 20182850
Nov. 24, 2020    (EP) ..................................... 20209617

(51) Int. Cl.
*C12N 15/82*        (2006.01)
*C12Q 1/68*         (2018.01)
*C12Q 1/6895*       (2018.01)

(52) U.S. Cl.
CPC ....... *C12N 15/8282* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

WO        2009/000736 A2    12/2008

OTHER PUBLICATIONS

Sebastiani et al (2017 Front Plant Sci May 30;8:922 (Year: 2017).*
Extended ESR for EP20182850.6, mailed on Nov. 18, 2020.
Oumouloud, All et al.: "Breeding melon for resistance to Fusarium wilt: recent developments", Euphytica, vol. 192(2), Jul. 1, 2013, pp. 155-169, XP055747186, NL, ISSN: 0014-2336.
Oumouloud, Ali et al.: "Development of 13-27 molecular markers linked to the Fom-1 locus for resistance to Fusarium race 2 in melon", Euphytica, Kluwer Academic Publishers, DO, vol. 164(2), Mar. 15, 2008, pp. 347-356, XP019641898, ISSN: 1573-5060.
Wang, Shiwei, et al: "Developments of functional markers for—mediated fusarium wilt resistance based on single nucleotide poly-morphism in melon (L.)", Molecular Breeding, Kluwer Academic Publishers, DO, vol. 27(3), Apr. 16, 2010, pp. 385-393, XP019886125, ISSN: 1572-9788.
Database EMBL [Online] Dec. 16, 2014, "Cucumis melo genomic scaffold, anchoredscaffold00035", XP002804075, retrieved from EBI Accession No. EM_STD:LN681870.
International Search Report for International Application No. PCT/EP2021/067539 mailed Sep. 16, 2021.
Database EMBL [Online] Dec. 16, 2014, "Cucumis melo genomic chromosome, ch_4", XP002804069, retrieved from EBI Accession No. EM_STD:LN713258.
Database EMBL [Online] Dec. 16, 2014, "Cucumis melo genomic scaffold, anchoredscaffold00011", XP002804068, retrieved from EBI Accession No. EM_STD:LN681841.
Risser et al., "A proposed nomenclature of *Fusarium oxysporum f. sp. melonis* races and resistance genes in cucumis melo," The American Phytopathological Society, (1976); 66: 1105-1106.
Perchepied, L. et al., "Strain-specific and recessive QTLs involved in the control of partial resistance to *Fusarium oxysporum f. sp. melonis* race 1.2 in a recombinant inbred line population of melon," Theor Appl Genet (2005) 111: 65-74.
Zink, F.W. et al., "Inheritance of Resistance in Muskmelon to Fusarium Wilt," J. Amer. Soc. Hort. Sci, (1985) 110(5):600-604.

* cited by examiner

*Primary Examiner* — Brent T Page
(74) *Attorney, Agent, or Firm* — Karen A. Magri

(57)        ABSTRACT

The present invention relates to novel melon plants displaying an increased resistance to *Fusarium oxysporum* f.sp. *melonis* race 1,2 infection. The present invention also relates to seeds and parts of said plants, for example fruits. The present invention further relates to methods of making and using such seeds and plants. The present invention also relates to novel genetic sequences associated with said increased resistance and to molecular markers associated with said novel genetic sequences.

19 Claims, 1 Drawing Sheet
Specification includes a Sequence Listing.

Pictures of a FOM 1,2 phenotyping test whereby symptoms are evaluated 11 (a), 13 (b), 15 (c), 18 (d), 20 (e) and 22 (f) days after inoculation.

a.

b.

c.

d.

e.

f.

SEQUENCE LISTING

```
<160> NUMBER OF SEQ ID NOS: 60

<210> SEQ ID NO 1
<211> LENGTH: 329
<212> TYPE: DNA
<213> ORGANISM: Cucumis melo
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (131)..(131)
```

<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t

<400> SEQUENCE: 1
acctccanaa aaatataata ttgatttact caaaggttaa gaaattgaaa attttgacat        60
attgacataa ngaatatact agtatttctt cactggnaaa catatgtcct ngataatttt       120
ggatcgagag ntttacaagc ctaaaagagg cncaatgcca atgataaact tggaatacat       180
tagtcatgtg agaacaaaaa aagtgcaaga aatgtaccaa cggaagaaca tgcaangnaa       240
aaaagaagaa atngagntga aagagncaaa tatagccatc tcgattgacc actttctttc       300
gtggaagtct attcttatct gtcgtagtc                                         329

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
ttgatttact caaaggttaa ga                                                  22

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
ctagtatttc ttcactgg                                                      18

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
actagtattt cttcactag                                                     19

<210> SEQ ID NO 5
<211> LENGTH: 18

```
<212> TYPE: DNA
<213> ORGANISM: Artificial Sequence
<220> FEATURE:
<223> OTHER INFORMATION: Synthetic

<400> SEQUENCE: 5
gacttccacg aaagaaag                                                        18

<210> SEQ ID NO 6
<211> LENGTH: 183
<212> TYPE: DNA
<213> ORGANISM: Cucumis melo
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t

<400> SEQUENCE: 6
ttgaagtaca tattgattaa agtgagagat gtgtgggttt tttgaggaaa acatgagtga        60
tacatttcat gtaattcctt ctttttacaa gttcnctatg aaagtttttat agaatttggg      120 gttctaattt gttttttttt ttanagggat atatggacca caagttcant atatattctc      180
cct                                                                     183

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
agtgagagat gtgtgggt                                                        18

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
ttagaacccc aaattcta                                                        18

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
aattagaacc ccaaatcct                                                       19

<210> SEQ ID NO 10
<211> LENGTH: 18
<212> TYPE: DNA
<213> ORGANISM: Artificial Sequence
<220> FEATURE:
```

<223> OTHER INFORMATION: Synthetic

<400> SEQUENCE: 10
ttgtggtcca tatatccc                                                             18

<210> SEQ ID NO 11
<211> LENGTH: 146
<212> TYPE: DNA
<213> ORGANISM: Cucumis melo
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t

<400> SEQUENCE: 11
nnnnnnntat atatatataa cattgctaat aatttgacgt tgaattgtaa tatgattggc      60
taaggaattg acaaaatctt tttnatatga agaatttnaa gttcaatgag agaaatcttt     120
ggtgcctttg tctcangagt aatata                                          146

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
cattgctaat aatttgacgt tg                                                22

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
tggctaagga attgacaa                                                     18

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
ttggctaagg aattgacg                                                     18

<210> SEQ ID NO 15
<211> LENGTH: 17
<212> TYPE: DNA
<213> ORGANISM: Artificial Sequence
<220> FEATURE:
<223> OTHER INFORMATION: Synthetic -continued

<400> SEQUENCE: 15
ggcaccaaag atttctc                                                17

<210> SEQ ID NO 16
<211> LENGTH: 308
<212> TYPE: DNA
<213> ORGANISM: Cucumis melo

<400> SEQUENCE: 16
tttaacctat ctctaatcat cctatcacat tggtatcatc taatcttaga cttgttgcca      60
tttttgaaaa tattaggttg aattgtttat tttgagagtt tgtttgattt tagttttctc     120
taattttggt ctttgtattt ttaataaagc ttaaattcag ttcattgaag ttcttatttt     180
tcaatcgaaa ttttgcaaga aaatataagg tggatatatt tttagatttt ataataaaga     240
tgctttttga gaaattcaac aataaattag tagggaatgg atttaaggtt aattaaaaat     300
atgaagaa                                                              308

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
cctatcacat tggtatcatc                                             20

<210> SEQ ID NO 18
<211> LENGTH: 19
<212> TYPE: DNA
<213> ORGANISM: Artificial Sequence
<220> FEATURE:
<223> OTHER INFORMATION: Synthetic

<400> SEQUENCE: 18
ttctcaaaaa gcatcttta                                              19

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
tgaatttctc aaaaagcatt                                             20

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
ccttaaatcc attccctact a                                           21

<210> SEQ ID NO 21
<211> LENGTH: 239
<212> TYPE: DNA
<213> ORGANISM: Cucumis melo
<220> FEATURE:

```
<221> NAME/KEY: misc_feature
<222> LOCATION: (73)..(75)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (150)..(153)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t

<400> SEQUENCE: 21
taaattagaa aattatgagg ggagtggtac tgtagtgaag atgttccaaa tgcattaata      60
taggattata atnnntataa aattaattct ctcttacatg tttgttttct tnaatataat     120
gtgtttttaa aaaatattct ccctcacatn nnnaaaaaaa aaaagaaaat tagaggatta     180
tcaaacatna atgtcttctn ggctaagtca tacgtttgaa tttgatattt gtgtgtata     239

<210> SEQ ID NO 22
<211> LENGTH: 18
<212> TYPE: DNA
<213> ORGANISM: Artificial Sequence
<220> FEATURE:
<223> OTHER INFORMATION: Synthetic

<400> SEQUENCE: 22
ggagtggtac tgtagtga                                                    18

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ataatcctct aattttcttt                                                  20

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
ataatcctct aattttctat t                                                21

<210> SEQ ID NO 25
<211> LENGTH: 19
<212> TYPE: DNA
<213> ORGANISM: Artificial Sequence
<220> FEATURE:
<223> OTHER INFORMATION: Synthetic

<400> SEQUENCE: 25
tcaaacgtat gacttagcc                                                   19
```

```
<210> SEQ ID NO 26
<211> LENGTH: 215
<212> TYPE: DNA
<213> ORGANISM: Cucumis melo
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (149)..(170)
<223> OTHER INFORMATION: n is a, c, g, or t

<400> SEQUENCE: 26
tctgggctnc ctgnatagta agccgggaac caccctttct tcataaacct ctattgttaa      60
aaagattgag aggngaatca aaatgtgggt gtcatcttaa atatccaatg gaggttaact     120
attattcaag ctagatcaag taatctcgnn nnnnnnnnnn nnnnnnnnnn caaactaccg     180
agtaaagttg caagcatgat cgaaaagctc tatag                               215

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
agccgggaac caccctttct t                                               21

<210> SEQ ID NO 28
<211> LENGTH: 24
<212> TYPE: DNA
<213> ORGANISM: Artificial Sequence
<220> FEATURE:
<223> OTHER INFORMATION: Synthetic

<400> SEQUENCE: 28
cataaacctc tattgttaaa aaga                                            24

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
cataaacctc tattgttaaa aaga                                            24

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
gcttgcaact ttactcggta gtttg                                           25
```

```
<210> SEQ ID NO 31
<211> LENGTH: 183
<212> TYPE: DNA
<213> ORGANISM: Cucumis melo

<400> SEQUENCE: 31
agtagattga gcaaaaaact ttgggccagg tacagttcat tgattttcct aaacatctct        60
cctaagtcat ttctctaggt tttttgtttc agtaaaaaag ttgagctagt ctgaattcat       120
aattcaataa tctgcagacc acgtgaagag cggaagacct tcttcttctt caatggaaat       180
ctt                                                                      183

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
ttgggccagg tacagttca                                                      19

<210> SEQ ID NO 33
<211> LENGTH: 23
<212> TYPE: DNA
<213> ORGANISM: Artificial Sequence
<220> FEATURE:
<223> OTHER INFORMATION: Synthetic

<400> SEQUENCE: 33
tgcagattat tgaattatga att                                                 23

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
tgcagattat tgaattacga attc                                                24

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
agaaggtctt ccgctcttca cg                                                  22

<210> SEQ ID NO 36
<211> LENGTH: 225
<212> TYPE: DNA
<213> ORGANISM: Cucumis melo
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
```

```
<222> LOCATION: (187)..(187)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t

<400> SEQUENCE: 36
aaaacgatta ggcctctttn acgaaaatcg ttaatttgaa agttactact aaagttttga        60
aagtatacat taacttaaaa atgctacttt tgctctagat attgagttct tggtgtttat       120
ttgtagagtg gaaatgtaaa nggaggattt tgaaatagag aagttcctaa aattcttaat       180
gcttctncca acttcaaccg ccattaaacc ctnacaaanc cctct                       225

<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37
acgaaaatcg ttaatttgaa agt                                               23

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
aaagttttga aagtatacat                                                   20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
aagttttgaa agtatacgtt                                                   20

<210> SEQ ID NO 40
<211> LENGTH: 17
<212> TYPE: DNA
<213> ORGANISM: Artificial Sequence
<220> FEATURE:
<223> OTHER INFORMATION: Synthetic

<400> SEQUENCE: 40
aatggcggtt gaagttg                                                      17

<210> SEQ ID NO 41
<211> LENGTH: 232
<212> TYPE: DNA
<213> ORGANISM: Cucumis melo
<220> FEATURE:
<221> NAME/KEY: misc_feature
<222> LOCATION: (230)..(231)
<223> OTHER INFORMATION: n is a, c, g, or t
```

-continued

```
<400> SEQUENCE: 41
atccctataa agtcacaaga gcctttcact aagttggctt catcctttgt aaaaatggggg      60 agttttgagc ctactatttt cttcatcaaa ttagaatagt ctccgaccat caatggatga     120
aggaccctgc attaaaccaa caataataaa caagaaggtt ttgtcaatat cgacatatat     180
agcttaatcg gtttccgcat atatctttga taaaagattt taggtcttcn ng             232

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
gcctttcact aagttggctt catc                                            24

<210> SEQ ID NO 43
<211> LENGTH: 23
<212> TYPE: DNA
<213> ORGANISM: Artificial Sequence
<220> FEATURE:
<223> OTHER INFORMATION: Synthetic

<400> SEQUENCE: 43
tttattattg ttggtttaat gca                                             23

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
tattattgtt ggcttaatgc a                                               21

<210> SEQ ID NO 45
<211> LENGTH: 25
<212> TYPE: DNA
<213> ORGANISM: Artificial Sequence
<220> FEATURE:
<223> OTHER INFORMATION: Synthetic

<400> SEQUENCE: 45
tatcaaagat atatgcggaa accga                                           25

<210> SEQ ID NO 46
<211> LENGTH: 163
<212> TYPE: DNA
<213> ORGANISM: Cucumis melo

<400> SEQUENCE: 46
taactctacg catctacttc ccaccctctc ttaataacat cctattcctt caaaatctaa      60
atgaatataa tccattctta cttattatct cttaattcac aaagaaatca ttgtactgca     120
aaattcacaa accatattcc aaaaaccctc ttagtaattg ctt                      163

<210> SEQ ID NO 47
<211> LENGTH: 21
<212> TYPE: DNA
<213> ORGANISM: Artificial Sequence
<220> FEATURE:
<223> OTHER INFORMATION: Synthetic
```

-continued

<400> SEQUENCE: 47
ccaccctctc ttaataacat c                                                                     21

<210> SEQ ID NO 48
<211> LENGTH: 18
<212> TYPE: DNA
<213> ORGANISM: Artificial Sequence
<220> FEATURE:
<223> OTHER INFORMATION: Synthetic

<400> SEQUENCE: 48
tttgcagtac aatgattt                                                                         18

<210> SEQ ID NO 49
<211> LENGTH: 17
<212> TYPE: DNA
<213> ORGANISM: Artificial Sequence
<220> FEATURE:
<223> OTHER INFORMATION: Synthetic

<400> SEQUENCE: 49
tttgcagtac aatgttt                                                                          17

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tttggaatat ggtttgtgaa                                                                       20

<210> SEQ ID NO 51
<211> LENGTH: 157
<212> TYPE: DNA
<213> ORGANISM: Cucumis melo
<220> FEATURE:
<221> NAME/KEY: misc_feature
<222> LOCATION: (53)..(53)
<223> OTHER INFORMATION: n is a, c, g, or t

<400> SEQUENCE: 51
ttagaatgtg ttttcaagga gggcaagaag gtaaatcagc aagagacggt tanaggtgca       60
gctgcaactg tacgtacgca aggggggacc aactctgtga ggggcgttaa gtagggtttt      120
gcaggtcaga ggaaggggggg gaatgttttt ggcagtg                              157

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
gggcaagaag gtaaatcagc aa                                                                    22

<210> SEQ ID NO 53
<211> LENGTH: 14
<212> TYPE: DNA
<213> ORGANISM: Artificial Sequence
<220> FEATURE:
<223> OTHER INFORMATION: Synthetic

```
<400> SEQUENCE: 53
taacgcccct caca                                                      14

<210> SEQ ID NO 54
<211> LENGTH: 16
<212> TYPE: DNA
<213> ORGANISM: Artificial Sequence
<220> FEATURE:
<223> OTHER INFORMATION: Synthetic

<400> SEQUENCE: 54
cttaacgtcc ctcaca                                                    16

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
cccttcctct gacctgcaaa                                                20

<210> SEQ ID NO 56
<211> LENGTH: 215
<212> TYPE: DNA
<213> ORGANISM: Cucumis melo

<400> SEQUENCE: 56
tgaaactagg tcattagcct agtttggctt cttctgggtt gttatttttg tagattcatc   60
tttctgtttt ggttctctag attgtattgg ccgaattgta tatttttct caatacaagc   120 tcgttctttt ttaaatcaaa acaatcattt tcccgtagta aaaagttggt actagaaacc   180
ataaggccca aagctagtca aaattataac agctg                              215

<210> SEQ ID NO 57
<211> LENGTH: 22
<212> TYPE: DNA
<213> ORGANISM: Artificial Sequence
<220> FEATURE:
<223> OTHER INFORMATION: Synthetic

<400> SEQUENCE: 57
agtttggctt cttctgggtt gt                                             22

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
ttggttctct agattgtatt                                                20

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
tggttctcta gcttgtat                                                  18
```

-continued

```
<210> SEQ ID NO 60
<211> LENGTH: 21
<212> TYPE: DNA
<213> ORGANISM: Artificial Sequence
<220> FEATURE:
<223> OTHER INFORMATION: Synthetic

<400> SEQUENCE: 60
agctttgggc cttatggttt c                                              21
```

DISEASE RESISTANT MELON PLANTS

RELATED APPLICATION INFORMATION

This application is a national stage entry under 35 U.S.C. § 371 of International Application No. PCT/EP2021/067539, filed 25 Jun. 2021, which claims the benefit of EP 20182850.6, filed 29 Jun. 2020, and EP 20209617.8 filed 24 Nov. 2020, the contents of which are incorporated herein by reference in their entireties.

STATEMENT REGARDING ELECTRONIC SUBMISSION OF A SEQUENCE LISTING

A Sequence Listing in ASCII text format, submitted under 37 C.F.R. § 1.821, entitled "81926-WO-REG-ORG-P-1_June2021_Sequence listing_ST25.txt", 16,305 bytes in size, generated on Nov. 22, 2022, and filed via EFS-Web is provided in lieu of a paper copy. This Sequence Listing is hereby incorporated by reference into the specification for its disclosures.

FIELD OF THE INVENTION

The present invention relates to novel melon plants displaying an increased resistance to *Fusarium oxysporum* f.sp. *melonis* race 1,2 infection. The present invention also relates to seeds and parts of said plants, for example fruits. The present invention further relates to methods of making and using such seeds and plants. The present invention also relates to novel genetic sequences associated with said increased resistance and to molecular markers associated with said novel genetic sequences.

BACKGROUND OF THE INVENTION

Plant pathogens are known to cause massive damage to important crops, resulting in significant agricultural losses with widespread consequences for both the food supply and other industries that rely on plant materials. As such, there is a long felt need to reduce the incidence and/or impact of agricultural pests on crop production.

An example of such pathogens is the *Fusarium oxysporum* genus of plant fungi. *F. oxysporum* is known to devastate various crop plants including, but not limited to pea, banana, cotton, tomato, melon and others. *F. oxysporum* is characterized by several different specialized forms, which are referred to as formae specialis (f.sp.), each of which infect a variety of hosts to cause disease. There are at least 48 different formae specialis of *F. oxysporum*.

One particular formae specialis of *F. oxysporum* is *F. oxysporum* f.sp. *melonis* (FOM), which infects various melons of the species *Cucumis melo*, which includes European cantaloupes and muskmelons such as American cantaloupes, sugar melons, honeydews, and Casaba as well as inodorous melons such as Piel de Sapo and Yellow Canari. Several races have been identified for FOM, and include races 0, 1, 2, and 1,2. Additionally, two genes, Fom-1, Fom-2 and Fom-3, have been identified that are associated with resistance to races 0 and 2, and 0 and 1, respectively (Risser et al., 1976; Zink and Gubler, 1985).

FOM 1,2 races are further classified according to the type of phenotype impact they generate on melon plants. Race 1,2 was further divided into two subraces: 1,2y, which causes leaf yellowing before wilting, and 1,2w, nonyellowing strains where wilting occurs without prior yellowing symptoms (Herman and Perl-Treves, 2007).

Some sources of resistance have been described against yellowing type FOM 1,2 races. For instance, WO2009/000736 describes melon plants comprising QTLs on chromosomes 3, 6, 7, 9 and 10 for increased resistance against FOM 1,2 yellowing strains. Perchepied et al. (2005) and Oumouloud et al. (2013) also reported some sources of resistance against both yellowing and wilting strains of FOM 1,2 but under polygenic control with multiple recessive QTLs being identified.

However, there remains a need for novel sources of resistance against FOM 1,2, in particular against FOM 1,2 wilting strains, which would provide for easier and better FOM 1,2 resistance management in commercial melon backgrounds.

SUMMARY OF THE INVENTION

The present invention addresses the need for an improved resistance to FOM 1,2 wilting strains by including and providing novel melon plants comprising an increased FOM 1,2 resistance trait. By identifying one QTL associated with increased FOM 1,2 resistance in a breeding population and by introgressing its corresponding sequence into elite melon plants, the FOM 1,2 resistance capability of the melon plant was greatly increased, which has a positive impact on overall plant performance. The FOM 1,2 resistance QTL and its corresponding introgressed sequence, located on chromosome 4 (QTL4), is of semi-dominant nature, hence one copy of the sequence already provides an improved FOM 1,2 resistance phenotype.

Altogether, the characteristics of the improved FOM 1,2 resistant melon plant disclosed within the present invention provide a melon grower with novel solutions to enhance economic and commercial efficiency when deploying melon varieties in a FOM 1,2 pressured field.

In a first embodiment, the invention provides a cultivated melon plant, preferably a cultivated *Cucumis melo* subsp. *melo* plant resistant to *Fusarium oxysporum* f.sp. *melonis* race 1,2 (FOM 1,2) infection, comprising in its genome an introgressed sequence from *C. melo* subsp. *agrestis* which confers resistance to FOM 1,2, wherein said introgressed sequence is located on chromosome 4 and comprises at least one of the following SNP markers:

a) a G genotype in the heterozygous or homozygous state for SNP marker 1 at a position corresponding to position 95 in SEQ ID NO: 1;

b) an A genotype in the heterozygous or homozygous state for SNP marker 2 at a position corresponding to position 113 in SEQ ID NO: 6;

c) an A genotype in the heterozygous or homozygous state for SNP marker 3 at a position corresponding to position 73 in SEQ ID NO: 11;

d) a G genotype in the heterozygous or homozygous state for SNP marker 4 at a position corresponding to position 239 in SEQ ID NO: 16;

e) an A genotype in the heterozygous or homozygous state for SNP marker 5 at a position corresponding to position 163 in SEQ ID NO: 21;

f) an A genotype in the heterozygous or homozygous state for SNP marker 6 at a position corresponding to position 59 in SEQ ID NO: 26;

g) an A genotype in the heterozygous or homozygous state for SNP marker 7 at a position corresponding to position 119 in SEQ ID NO: 31;

h) an A genotype in the heterozygous or homozygous state for SNP marker 8 at a position corresponding to position 69 in SEQ ID NO: 36;

i) an A genotype in the heterozygous or homozygous state for SNP marker 9 at a position corresponding to position 136 in SEQ ID NO: 41; and/or j) a T genotype in the heterozygous or homozygous state for SNP marker 10 at a position corresponding to position 108 in SEQ ID NO: 46.

In a further embodiment of the invention, said FOM 1,2 resistance-conferring introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41 and/or SEQ ID NO: 46, or a sequence that is at least 80%, preferably at least 85%, more preferably at least 90%, even more preferably at least 95% identical to one or more of said sequences.

In a further embodiment of the invention, said plant is heterozygous for said at least one SNP marker. In a further embodiment of the invention, said plant is homozygous for said at least one SNP marker.

In a further embodiment of the invention, said FOM 1,2 resistance-conferring introgressed sequence confers resistance upon FOM 1,2 wilting strains.

In a further embodiment of the invention, said introgressed sequence is comprised in melon line 19MFR011167, representative seed of which is deposited under NCIMB Accession No. 43448, or a progeny or an ancestor thereof.

In a further embodiment, the invention provides a plant according to any of the preceding embodiments wherein said plant is obtained by crossing melon line 19MFR011167, representative seed of which is deposited under NCIMB Accession No. 43448, or a progeny or an ancestor thereof, with a melon plant that does not contain said FOM 1,2 resistance-conferring introgressed sequence.

In a further embodiment, the invention provides a plant according to any of the preceding embodiments, wherein said plant is an inbred, a dihaploid or a hybrid plant.

It is a further embodiment to provide a plant part, organ or tissue obtainable from a melon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the FOM 1,2 resistance according to the invention, particularly when grown into a plant that produces fruits.

In a further embodiment, the invention provides a seed that produces a plant according to any of the preceding embodiments.

In a further embodiment, the invention provides a method for producing a cultivated melon plant, preferably a cultivated *Cucumis melo* subsp. *melo* plant, exhibiting resistance to FOM 1,2 comprising the steps of a) crossing a plant according to any one of the preceding embodiments with a cultivated melon plant lacking said FOM 1,2 resistance-conferring introgressed sequence;

b) selecting a progeny plant comprising said introgressed sequence located on chromosome 4 conferring resistance to FOM 1,2, said selecting step comprising detecting at least one of the following SNP markers:

i) a G genotype in the heterozygous or homozygous state for SNP marker 1 at a position corresponding to position 95 in SEQ ID NO: 1;

ii) an A genotype in the heterozygous or homozygous state for SNP marker 2 at a position corresponding to position 113 in SEQ ID NO: 6;

iii) an A genotype in the heterozygous or homozygous state for SNP marker 3 at a position corresponding to position 73 in SEQ ID NO: 11;

iv) a G genotype in the heterozygous or homozygous state for SNP marker 4 at a position corresponding to position 239 in SEQ ID NO: 16;

v) an A genotype in the heterozygous or homozygous state for SNP marker 5 at a position corresponding to position 163 in SEQ ID NO: 21;

vi) an A genotype in the heterozygous or homozygous state for SNP marker 6 at a position corresponding to position 59 in SEQ ID NO: 26;

vii) an A genotype in the heterozygous or homozygous state for SNP marker 7 at a position corresponding to position 119 in SEQ ID NO: 31;

viii) an A genotype in the heterozygous or homozygous state for SNP marker 8 at a position corresponding to position 69 in SEQ ID NO: 36;

ix) an A genotype in the heterozygous or homozygous state for SNP marker 9 at a position corresponding to position 136 in SEQ ID NO: 41; and/or x) a T genotype in the heterozygous or homozygous state for SNP marker 10 at a position corresponding to position 108 in SEQ ID NO: 46;

thereby producing a plant with enhanced resistance to FOM 1,2.

In a further embodiment, the invention relates to the method of any of the preceding embodiments, wherein the method further comprises:

c) selfing the selected progeny or crossing the selected progeny with another melon plant to produce further progeny.

In a further embodiment, the invention relates to the method of the preceding embodiment, wherein further progeny are selected and selfed/crossed for 2 to 10 more generations.

In a further embodiment, the invention relates to the method of any of the preceding embodiments, wherein the plant of step a) is melon line 19MFR011167, representative seed of which is deposited under NCIMB Accession No. 43448, or a progeny or an ancestor thereof.

In a further embodiment, the invention relates to a method for producing a F1 melon plant exhibiting resistance to FOM 1,2, the method comprising crossing an inbred melon plant, which is a plant according to any one of the preceding embodiments, with a different inbred melon plant to produce F1 hybrid progeny.

In a further embodiment, the invention provides a method for identifying a cultivated melon plant, preferably a cultivated *Cucumis melo* plant, exhibiting resistance to FOM 1,2 and having at least one copy of said FOM 1,2 resistance-conferring introgressed sequence, said method comprising the step of detecting at least one of the following SNP markers:

a) a G genotype in the heterozygous or homozygous state for SNP marker 1 at a position corresponding to position 95 in SEQ ID NO: 1;

b) an A genotype in the heterozygous or homozygous state for SNP marker 2 at a position corresponding to position 113 in SEQ ID NO: 6;

c) an A genotype in the heterozygous or homozygous state for SNP marker 3 at a position corresponding to position 73 in SEQ ID NO: 11;

d) a G genotype in the heterozygous or homozygous state for SNP marker 4 at a position corresponding to position 239 in SEQ ID NO: 16;

e) an A genotype in the heterozygous or homozygous state
for SNP marker 5 at a position corresponding to position 163 in SEQ ID NO: 21;

f) an A genotype in the heterozygous or homozygous state
for SNP marker 6 at a position corresponding to position 59 in SEQ ID NO: 26;

g) an A genotype in the heterozygous or homozygous state
for SNP marker 7 at a position corresponding to position 119 in SEQ ID NO: 31;

h) an A genotype in the heterozygous or homozygous state
for SNP marker 8 at a position corresponding to position 69 in SEQ ID NO: 36;

i) an A genotype in the heterozygous or homozygous state
for SNP marker 9 at a position corresponding to position 136 in SEQ ID NO: 41; and/or j) a T genotype in the heterozygous or homozygous state
for SNP marker 10 at a position corresponding to position 108 in SEQ ID NO: 46;

thereby identifying a melon plant exhibiting resistance to FOM 1,2.

In a further embodiment, the invention relates to the method of the preceding embodiment, wherein said method further comprises selecting a melon plant comprising said one or more SNP markers, and crossing the selected melon plant with a second melon plant to produce progeny melon plants that comprise at least one of said SNP markers and exhibits increased resistance to FOM 1,2.

BRIEF DESCRIPTION OF THE DRAWINGS

FIG. 1 shows pictures of a FOM 1,2 phenotyping test whereby symptoms are evaluated 11 (a), 13 (b), 15 (c), 18 (d), 20 (e) and 22 (f) days after inoculation.

DETAILED DESCRIPTION OF THE INVENTION

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "cultivated melon" or an "elite melon" plant is understood within the scope of the invention to refer to a plant that is no longer in the natural state but has been developed and domesticated by human care and for agricultural use and/or human consumption, and excludes wild melon accessions, such as *C. melo* subsp. *agrestis* accessions. As a matter of example, in embodiments, a cultivated or elite melon plant according to the present invention is capable of growing fruits having orange flesh and/or a Brix level better than 6, preferably better than 12. Alternatively, or additionally, the cultivated melon plant is a hybrid plant. Alternatively, or additionally, the cultivated melon plant is a *C. melo* subsp. *melo* plant. In the context of an interspecific cross between a *C. melo* subsp. *melo* plant and a wild melon accession, a cultivated melon plant is defined as a progeny plant of said interspecific cross, wherein said progeny plant has been backcrossed at least three times against a *C. melo* subsp. *melo* plant.

An "allele" is understood within the scope of the invention to refer to alternative or variant forms of various genetic units identical or associated with different forms of a gene or of any kind of identifiable genetic determinant such as a QTL, which are alternative in inheritance because they are situated at the same locus in homologous chromosomes.

Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

Relatively speaking, the term "improved FOM 1,2 resistance" or "increased FOM 1,2 resistance" is herein understood to mean that a plant according to the present invention, e.g. comprising an introgressed sequence from *C. melo* subsp. *agrestis* plant which confers resistance to FOM 1,2, wherein said introgressed sequence is located on chromosome 4 and comprising at least one of SNP markers 1 to 10, is more tolerant or more resistant to FOM 1,2 wilting strains when compared with a plant lacking said introgressed sequence.

"Improved FOM 1,2 resistance" is understood within the scope of the invention to mean a melon plant which has a statistically significant improved resistance to FOM 1,2 wilting strains compared to a control melon plant lacking the introgressed sequence of the invention (for example as described in the Example section), using standard error and/or at $P<0.05$ or $P<0.01$ using Student's test.

"Phenotype" is understood within the scope of the invention to refer to a distinguishable characteristic(s) of a genetically controlled trait.

A "control melon plant" is understood within the scope of the invention to mean a melon plant that has the same genetic background as the cultivated melon plant of the present invention wherein the control plant does not have the introgressed sequence of the present invention linked to improved FOM 1,2 resistance. In particular a control melon plant is a melon plant belonging to the same plant variety and does not comprise the introgressed sequence of the present invention. The control melon plant is grown for the same length of time and under the same conditions as the cultivated melon plant of the present invention. Plant variety is herein understood according to definition of UPOV.

Thus a control melon plant may be a near-isogenic line, an inbred line or a hybrid provided that they have the same genetic background as the melon plant of the present invention except the control plant does not have the introgressed sequence of the present invention linked to improved FOM 1,2 resistance.

The term "trait" refers to a characteristic or a phenotype. In the context of the present invention, a FOM 1,2 resistance trait is an improved FOM 1,2 resistance trait. A trait may be inherited in a dominant or recessive manner, or in a partial or incomplete-dominant manner. In the context of the present invention, the FOM 1,2 resistance-conferring introgressed sequence located on chromosome 4 is semi-dominant. A melon plant of the invention can therefore be homozygous or heterozygous for the trait. Furthermore, a trait may be monogenic or polygenic, or may result from the interaction of one or more genes with the environment. In the context of the present invention, the FOM 1,2 resistance-conferring introgressed sequence located on chromosome 4 is sufficient to confer, alone, the improved FOM 1,2 resistance trait.

The terms "hybrid", "hybrid plant", and "hybrid progeny" refer to an individual produced from genetically different parents (e.g. a genetically heterozygous or mostly heterozygous individual).

The term "inbred line" refers to a genetically homozygous or nearly homozygous population. An inbred line, for example, can be derived through several cycles of brother/sister breeding or of selfing or in dihaploid production.

The term "dihaploid line" refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially no longer segregating (stable).

The term "genetically fixed" refers to a genetic sequence which has been stably incorporated into the genome of a plant that normally does not contain said genetic sequence. When genetically fixed, the genetic sequence can be transmitted in an easy and predictable manner to other plants by sexual crosses.

The term "rootstock" refers to a plant used as a receptacle for a scion plant. Typically, the rootstock plant and the scion plant are of different genotypes. In embodiments, plants according to the present invention are used as rootstock plants.

The term "plant" or "plant part" refers hereinafter to a plant part, organ or tissue obtainable from a melon plant according to the invention, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the improved FOM 1,2 resistance trait according to the invention, particularly when grown into a plant that produces fruits.

A "plant" is any plant at any stage of development.

A melon plant seed is a seed which grows into a melon plant according to any of the embodiments.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes. In the context of the invention, a melon plant comprising two identical copies of a particular introgressed sequence at a particular locus, e.g. the introgressed sequence located on chromosome 4, is homozygous on a corresponding locus.

"Heterozygous" is understood within the scope of the invention to refer to unlike alleles at one or more corresponding loci on homologous chromosomes. In the context of the invention, a melon plant comprising one copy of a particular introgressed sequence at a particular locus, e.g. the introgressed sequence located on chromosome 4, is heterozygous on a corresponding locus.

A "dominant" allele is understood within the scope of the invention to refer to an allele which determines the phenotype when present in the heterozygous or homozygous state.

A "semi-dominant" allele is understood within the scope of the invention to refer to an allele which determines the phenotype when present in the heterozygous or homozygous state. The intensity of the phenotype is however generally higher when the allele is present in the homozygous state.

A "recessive" allele refers to an allele which determines the phenotype when present in the homozygous state only.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene, a QTL or its corresponding genetic sequence contributing to a trait.

As used herein, "marker locus" refers to a region on a chromosome, which comprises a nucleotide or a polynucleotide sequence that is present in an individual's genome and that is associated with one or more loci of interest, which may comprise a gene or any other genetic determinant or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. The term "associated with" can be used with an equal meaning.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" or "DNA marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

As used herein, the term "genotype" refers to the genetic constitution of a cell or organism. An individual's "genotype for a set of genetic markers" includes the specific alleles, for one or more genetic marker loci, present in the individual's haplotype.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the F1, the F2, or any subsequent generation.

As used herein, the terms "quantitative trait locus" (QTL) refer to an association between a genetic marker and a chromosomal region and/or gene and/or introgressed sequence that affects the phenotype of a trait of interest. Typically, this is determined statistically; e.g., based on one or more methods published in the literature. A QTL can be a chromosomal region and/or a genetic locus with at least two alleles that differentially affect a phenotypic trait.

The term "recipient melon plant" is used herein to indicate a melon plant that is to receive DNA obtained from a donor melon plant that comprises an introgressed sequence for improved FOM 1,2 resistance.

The term "natural genetic background" is used herein to indicate the original genetic background of genetic sequence. Such a background may for instance be the genome of a wild accession of melon. For instance, the genetic sequence of the present invention was found at a specific location on chromosome 4 of a *C. melo* subsp. *agrestis* plant. Conversely, a method that involves the transfer of DNA, via e.g. breeding, comprising this genetic sequence from chromosome 4 of *C. melo* subsp. *agrestis* plant to the same position on chromosome 4 of another melon species, preferably a cultivated melon plant, even more preferably a *C. melo* subsp. *melo* plant, will result in this genetic sequence not being in its natural genetic background. When the genetic sequence of the present invention is transferred from a *C. melo* subsp. *agrestis* background into another melon species, preferably a cultivated melon plant, even more preferably a *C. melo* subsp. *melo* plant, they are referred to as "introgressed sequence" or "introgressed genetic sequence". A "donor melon plant" is understood within the scope of the invention to mean the melon plant which provides the introgressed sequence for improved FOM 1,2 resistance.

"Marker-based selection" is understood within the scope of the invention to refer to e.g. the use of genetic markers to detect one or more nucleic acids from the plant, where the nucleic acid is associated with a desired trait to identify plants that carry alleles for desirable (or undesirable) traits, so that those plants can be used (or avoided) in a selective breeding program.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (i.e. amplified sequence or target), one or more labelled allele-specific oligonucleotide probes and a detection system that records and interprets the hybridization signal. The presence or absence of the desired SNP marker allele may be determined by real-time PCR using double-stranded DNA dyes or the fluorescent reporter probe method.

"PCR (Polymerase chain reaction)" is understood within the scope of the invention to refer to a method of producing relatively large amounts of specific regions of DNA or subset(s) of the genome, thereby making possible various analyses that are based on those regions. "PCR primer" is understood within the scope of the invention to refer to relatively short fragments of single-stranded DNA used in the PCR amplification of specific regions of DNA.

"Probe" as used herein refers to a group of atoms or molecules which is capable of recognising and binding to a specific target molecule or cellular structure and thus allowing detection of the target molecule or structure. Particularly, "probe" refers to a labelled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Identity". The terms "identical" or "identity" in the context of two or more nucleic acid or protein sequences, refer to two or more sequences or sub-sequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequence of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The "thermal melting point" is the temperature (under defined ionic strength and pH) at which 50% of the target sequence hybridizes to a perfectly matched probe. Very stringent conditions are selected to be equal to the melting temperature ($T_m$) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.01M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

EMBODIMENTS

Plants, Seeds, Fruits.

In a first embodiment, the invention provides a cultivated melon plant, preferably a cultivated *Cucumis melo* subsp. *melo* plant resistant to *Fusarium oxysporum* f.sp. *melonis* race 1,2 (FOM 1,2) infection, comprising in its genome an introgressed sequence from *C. melo* subsp. *agrestis* which confers resistance to FOM 1,2, wherein said introgressed sequence is located on chromosome 4 and comprises at least one of the following SNP markers:

a) a G genotype in the heterozygous or homozygous state for SNP marker 1 in SEQ ID NO: 1;

b) an A genotype in the heterozygous or homozygous state for SNP marker 2 in SEQ ID NO: 6;

c) an A genotype in the heterozygous or homozygous state for SNP marker 3 in SEQ ID NO: 11;

d) a G genotype in the heterozygous or homozygous state for SNP marker 4 in SEQ ID NO: 16;

e) an A genotype in the heterozygous or homozygous state for SNP marker 5 in SEQ ID NO: 21;

f) an A genotype in the heterozygous or homozygous state for SNP marker 6 in SEQ ID NO: 26;

g) an A genotype in the heterozygous or homozygous state for SNP marker 7 in SEQ ID NO: 31;

h) an A genotype in the heterozygous or homozygous state for SNP marker 8 in SEQ ID NO: 36;

i) an A genotype in the heterozygous or homozygous state for SNP marker 9 in SEQ ID NO: 41; and/or j) a T genotype in the heterozygous or homozygous state for SNP marker 10 in SEQ ID NO: 46.

Further, the plant of the previous embodiment wherein:

a) the G genotype for SNP marker 1 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;

b) the A genotype for SNP marker 2 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;

c) the A genotype for SNP marker 3 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13;

d) the G genotype for SNP marker 4 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18;

e) the A genotype for SNP marker 5 can be identified in a PCR by amplification of a nucleic acid fragment with a pair of oligonucleotide primers: forward primer of SEQ ID NO: 22 and reverse primer of SEQ ID NO: 25, and probe of SEQ ID NO: 23;

f) the A genotype for SNP marker 6 can be identified in a PCR by amplification of a nucleic acid fragment with a pair of oligonucleotide primers: forward primer of SEQ ID NO: 27 and reverse primer of SEQ ID NO: 30, and probe of SEQ ID NO: 28;

g) the A genotype for SNP marker 7 can be identified in a PCR by amplification of a nucleic acid fragment with a pair of oligonucleotide primers: forward primer of SEQ ID NO: 32 and reverse primer of SEQ ID NO: 35, and probe of SEQ ID NO: 33;

h) the A genotype for SNP marker 8 can be identified in a PCR by amplification of a nucleic acid fragment with a pair of oligonucleotide primers: forward primer of SEQ ID NO: 37 and reverse primer of SEQ ID NO: 40, and probe of SEQ ID NO: 38;

i) the A genotype for SNP marker 9 can be identified in a PCR by amplification of a nucleic acid fragment with a pair of oligonucleotide primers: forward primer of SEQ ID NO: 42 and reverse primer of SEQ ID NO: 45, and probe of SEQ ID NO: 43; and/or j) the T genotype for SNP marker 10 can be identified in a PCR by amplification of a nucleic acid fragment with a pair of oligonucleotide primers: forward primer of SEQ ID NO: 47 and reverse primer of SEQ ID NO: 50, and probe of SEQ ID NO: 48.

In a further embodiment of the invention, said FOM 1,2 resistance-conferring introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41 and/or SEQ ID NO: 46, or a sequence that is at least 80%, preferably at least 85%, more preferably at least 90%, even more preferably at least 95% identical to one or more of said sequences while retaining corresponding SNP marker 1 to 10.

In a further embodiment of the invention, said plant is heterozygous for said at least one SNP marker. In a further embodiment of the invention, said plant is homozygous for said at least one SNP marker.

In a further embodiment of the invention, said FOM 1,2 resistance-conferring introgressed sequence confers increased resistance upon FOM 1,2 wilting strains.

In a further embodiment of the invention, said introgressed sequence is comprised in, is obtained from, or is obtainable from melon line 19MFR011167, representative seed of which is deposited under NCIMB Accession No. 43448, or a progeny or an ancestor thereof.

In a further embodiment, the invention provides a plant according to any of the preceding embodiments wherein said plant is obtained by crossing melon line 19MFR011167, representative seed of which is deposited under NCIMB Accession No. 43448, or a progeny or an ancestor thereof, with a melon plant that does not contain said FOM 1,2 resistance-conferring introgressed sequence.

In a further embodiment, the invention provides a plant according to any of the preceding embodiments, wherein said plant is an inbred, a dihaploid or a hybrid plant.

In another embodiment, the plant according to the invention is male sterile. In another embodiment, the plant according to the invention is cytoplasmic male sterile.

In another embodiment, the plant according to the invention grows mature melon fruits, wherein the interior flesh of said mature fruits is orange.

In a further embodiment, the melon plant of the invention is a melon plant according to any of preceding embodiments, wherein said FOM 1,2 resistance-conferring introgressed sequence located on chromosome 4 can be identified using any of the SNP markers 1 to 10 disclosed in Table 5 hereinbelow.

In a further embodiment, the invention provides a cultivated melon plant, preferably a cultivated *Cucumis melo* subsp. *melo* plant resistant to *Fusarium oxysporum* f.sp. *melonis* race 1,2 (FOM 1,2) infection, comprising in its genome an introgressed sequence from *C. melo* subsp. *agrestis* which confers resistance to FOM 1,2 located on chromosome 4, wherein said plant genome comprises:

a) an A genotype in the heterozygous or homozygous state for SNP marker 11 at a position corresponding to position 104 in SEQ ID NO: 51;

b) a C genotype in the heterozygous or homozygous state for SNP marker 12 at a position corresponding to position 81 in SEQ ID NO: 66; and c) at least one of the resistant alleles of the SNP markers 1 to 10 disclosed in Table 5.

In a further embodiment, the melon plant of the invention is a melon plant according to any of the preceding embodiments, wherein melon line 19MFR011167, or a progeny or an ancestor thereof, is the source of said FOM 1,2 resistance-conferring introgressed sequence, and wherein a representative seed of line 19MFR011167 has been deposited under NCIMB Accession No. 43448.

It is a further embodiment to provide a plant part, organ or tissue obtainable from a melon plant according to any of preceding embodiments, including but not limiting to leaves, stems, roots, flowers or flower parts, fruits, shoots, gametophytes, sporophytes, pollen, anthers, microspores, egg cells, zygotes, embryos, meristematic regions, callus tissue, seeds, cuttings, cell or tissue cultures or any other part or product of the plant which still exhibits the FOM 1,2 resistance according to the invention, particularly when grown into a plant that produces fruits.

In a further embodiment, the invention provides a seed that produces a plant according to any of the preceding embodiments.

In a further embodiment the invention relates to the use of a melon plant according to any of the preceding embodiments as a melon rootstock. In a further embodiment the invention relates to the use of melon line 19MFR011167, representative seed of which is deposited under NCIMB Accession No. 43448, or a progeny or an ancestor thereof as a melon rootstock.

In another embodiment is considered the use of a melon plant, plant part or seed according to any of the preceding embodiments for producing and harvesting melon fruits.

In another embodiment the invention relates to the use of a melon plant, plant part or seed according to any embodiments, wherein the melon plant, plant part or seed is melon line 19MFR011167, representative seed of which is deposited under NCIMB Accession No. 43448, or a progeny or an ancestor thereof.

In a further embodiment the invention relates to the use of a melon plant, plant part or seed according to any of the preceding embodiments to sow a field, a greenhouse, or a plastic house.

In one embodiment, the invention provides melon fruits produced by a melon plant according to any of the preceding embodiments.

The invention further relates to the use of a melon plant according to any of the preceding embodiments to introgress a FOM 1,2 resistance trait into a melon plant lacking said FOM 1,2 resistance trait.

The invention further relates to a melon plant according to any of the preceding embodiments, wherein said plant further comprises a QTL associated with increased resistance to yellowing FOM 1,2 strain, wherein said QTL is located on chromosome 9. In a further embodiment, said QTL is as disclosed in WO2009/000736.

Genetic Sequences, Markers.

The present invention is further directed to an introgressed genetic sequence linked to the FOM 1,2 resistance trait in the melon plant. In a further embodiment, the genetic sequence of the present invention is located on chromosome 4. In a further embodiment of the present invention, the genetic sequence is comprised in, obtained from or obtainable from a donor plant of melon line 19MFR011167, representative seed of which is deposited under NCIMB Accession No. 43448, or a progeny or an ancestor thereof, and comprising said genetic sequence.

In another embodiment, the introgressed genetic sequence of the present invention is located on chromosome 4 and is characterized by at least of the following SNP markers:

a) a G genotype in the heterozygous or homozygous state for SNP marker 1 in SEQ ID NO:1;

b) an A genotype in the heterozygous or homozygous state for SNP marker 2 in SEQ ID NO: 6;

c) an A genotype in the heterozygous or homozygous state for SNP marker 3 in SEQ ID NO: 11;

d) a G genotype in the heterozygous or homozygous state for SNP marker 4 in SEQ ID NO: 16;

e) an A genotype in the heterozygous or homozygous state for SNP marker 5 in SEQ ID NO: 21;

f) an A genotype in the heterozygous or homozygous state for SNP marker 6 in SEQ ID NO: 26;

g) an A genotype in the heterozygous or homozygous state for SNP marker 7 in SEQ ID NO: 31;

h) an A genotype in the heterozygous or homozygous state for SNP marker 8 in SEQ ID NO: 36;

i) an A genotype in the heterozygous or homozygous state for SNP marker 9 in SEQ ID NO: 41; and/or j) a T genotype in the heterozygous or homozygous state for SNP marker 10 in SEQ ID NO: 46.

The present invention discloses a kit for the detection of the FOM 1,2 resistance trait in a melon plant, particularly a cultivated melon plant, wherein said kit comprises at least one PCR oligonucleotide primer pair and probe, selected from:

a) forward primer of SEQ ID NO: 2 and reverse primer of SEQ ID NO: 5, and probe of SEQ ID NO: 3;

b) forward primer of SEQ ID NO: 7 and reverse primer of SEQ ID NO: 10, and probe of SEQ ID NO: 8;

c) forward primer of SEQ ID NO: 12 and reverse primer of SEQ ID NO: 15, and probe of SEQ ID NO: 13;

d) forward primer of SEQ ID NO: 17 and reverse primer of SEQ ID NO: 20, and probe of SEQ ID NO: 18;

e) forward primer of SEQ ID NO: 22 and reverse primer of SEQ ID NO: 25, and probe of SEQ ID NO: 23;

f) forward primer of SEQ ID NO: 27 and reverse primer of SEQ ID NO: 30, and probe of SEQ ID NO: 28;

g) forward primer of SEQ ID NO: 32 and reverse primer of SEQ ID NO: 35, and probe of SEQ ID NO: 33;

h) forward primer of SEQ ID NO: 37 and reverse primer of SEQ ID NO: 40, and probe of SEQ ID NO: 38;

i) forward primer of SEQ ID NO: 42 and reverse primer of SEQ ID NO: 45, and probe of SEQ ID NO: 43;

j) forward primer of SEQ ID NO: 47 and reverse primer of SEQ ID NO: 50, and probe of SEQ ID NO: 48.

The present invention also discloses the use of at least one, at least two or at least three of the SNP markers according to the invention for diagnostic selection and/or genotyping of the FOM 1,2 resistance trait locus in a melon plant, particularly a cultivated melon plant, The present invention further discloses the use of at least one, at least two or at least three of the SNP markers according to the invention for identifying in a melon plant, particularly a cultivated melon plant, more particularly a melon plant according to the invention, the presence of the FOM 1,2 resistance trait and/or for monitoring the introgression of the FOM 1,2 resistance trait in a melon plant, particularly a cultivated melon plant, particularly a melon plant according to the invention and as described herein. The invention further discloses a polynucleotide (amplification product) obtainable in a PCR reaction involving at least one oligonucleotide primer or a pair of PCR oligonucleotide primers selected from Table 5, which amplification product corresponds to an amplification product obtainable from melon line 19MFR011167, representative seed of which is deposited under NCIMB Accession No. 43448, or a progeny or an ancestor thereof, comprising the FOM 1,2 resistance-conferring introgressed sequence of the invention.

Also contemplated herein is a polynucleotide that has at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the FOM 1,2 resistance trait locus.

The present invention therefore further relates in one embodiment to derived markers, particularly to derived primers or probes, developed from an amplification product according to the invention and as described herein above by methods known in the art, which derived markers are genetically linked to the FOM 1,2 resistance trait locus.

Methods of Breeding.

In a further embodiment, the invention provides a method for producing a cultivated melon plant, preferably a cultivated *Cucumis melo* subsp. *melo* plant, exhibiting resistance to FOM 1,2 comprising the steps of a) crossing a plant according to any one of the preceding embodiments with a cultivated melon plant lacking said FOM 1,2 resistance-conferring introgressed sequence;

b) selecting a progeny plant comprising said introgressed sequence located on chromosome 4 conferring resistance to FOM 1,2, said selecting step comprising detecting at least one of the following SNP markers:

i) a G genotype in the heterozygous or homozygous state for SNP marker 1 in SEQ ID NO: 1;

ii) an A genotype in the heterozygous or homozygous state for SNP marker 2 in SEQ ID NO: 6;

iii) an A genotype in the heterozygous or homozygous state for SNP marker 3 in SEQ ID NO: 11;

iv) a G genotype in the heterozygous or homozygous state for SNP marker 4 in SEQ ID NO: 16;

v) an A genotype in the heterozygous or homozygous state for SNP marker 5 in SEQ ID NO: 21;

vi) an A genotype in the heterozygous or homozygous state for SNP marker 6 in SEQ ID NO: 26;

vii) an A genotype in the heterozygous or homozygous state for SNP marker 7 in SEQ ID NO: 31;

viii) an A genotype in the heterozygous or homozygous state for SNP marker 8 in SEQ ID NO: 36;

ix) an A genotype in the heterozygous or homozygous state for SNP marker 9 in SEQ ID NO: 41; and/or x) a T genotype in the heterozygous or homozygous state for SNP marker 10 in SEQ ID NO: 46;

thereby producing a plant with enhanced resistance to FOM 1,2.

In a further embodiment, the invention relates to the method of any of the preceding embodiments, wherein the method further comprises:

c) selfing the selected progeny or crossing the selected progeny with another melon plant to produce further progeny.

In a further embodiment, the invention relates to the method of the preceding embodiment, wherein further progeny are selected and selfed/crossed for 2 to 10 more generations.

In a further embodiment, the invention relates to the method of any of the preceding embodiments, wherein the plant of step a) is melon line 19MFR011167, representative seed of which is deposited under NCIMB Accession No. 43448, or a progeny or an ancestor thereof.

In another embodiment the invention relates to a method of providing a FOM 1,2 resistant melon plant, plant part or seed, wherein said method comprises the following steps:

a) Crossing a 1$^{st}$ plant lacking the FOM 1,2 resistance-conferring introgressed sequence of the invention with a 2$^{nd}$ melon plant according to any embodiments, b) Obtaining a progeny melon plant, and, c) Optionally, selecting a plant of said progeny characterized in that said plant exhibits resistance to FOM 1,2, particularly resistance to FOM 1,2 wilting strain.

In a further embodiment the invention relates to the method of the preceding embodiment wherein the 2$^{nd}$ melon plant is melon line 19MFR011167, representative seed of which is deposited under NCIMB Accession No. 43448, or a progeny or an ancestor thereof.

In another embodiment the invention relates to a method for producing a FOM 1,2 resistant melon plant comprising the following steps:

a) Providing seeds of a melon plant according to any of the preceding embodiments, b) Germinating said seed and growing a mature, fertile plant therefrom, c) Inducing self-pollination of said plant under a), growing fruits and harvesting the fertile seeds therefrom, and d) Growing plants from the seeds harvested under c) and selecting a FOM 1,2 resistant melon plant.

In another embodiment the invention relates to a method for increasing the resistance to FOM 1,2 of a melon plant, comprising the steps of:

a) selecting a melon, which comprises a FOM 1,2 resistance trait associated with one introgressed sequence located on chromosome 4, wherein said trait can be identified by the presence of at least one of the SNP markers listed in Table 5;

b) crossing said plant of step a), which comprises a FOM 1,2 resistance trait, with a melon plant, particularly a cultivated melon plant, which does not comprise a FOM 1,2 resistance trait and shows susceptibility to FOM 1,2, as compared to the plant of step a), and c) selecting progeny from said cross which shows increased FOM 1,2 resistance, as compared to the plant of step b).

In a further embodiment, the invention relates to a method for producing a F1 melon plant exhibiting resistance to FOM 1,2, the method comprising crossing an inbred melon plant, which is a plant according to any one of the preceding embodiments, with a different inbred melon plant to produce F1 hybrid progeny.

Methods of Selection.

In a further embodiment, the invention provides a method for identifying a cultivated melon plant, preferably a cultivated *Cucumis melo* plant, exhibiting resistance to FOM 1,2 and having at least one copy of said FOM 1,2 resistance-conferring introgressed sequence, said method comprising the step of detecting at least one of the following SNP markers:

a) a G genotype in the heterozygous or homozygous state for SNP marker 1 in SEQ ID NO: 1;

b) an A genotype in the heterozygous or homozygous state for SNP marker 2 in SEQ ID NO: 6;

c) an A genotype in the heterozygous or homozygous state for SNP marker 3 in SEQ ID NO: 11;

d) a G genotype in the heterozygous or homozygous state for SNP marker 4 in SEQ ID NO: 16;

e) an A genotype in the heterozygous or homozygous state for SNP marker 5 in SEQ ID NO: 21;

f) an A genotype in the heterozygous or homozygous state for SNP marker 6 in SEQ ID NO: 26;

g) an A genotype in the heterozygous or homozygous state for SNP marker 7 in SEQ ID NO: 31;

h) an A genotype in the heterozygous or homozygous state for SNP marker 8 in SEQ ID NO: 36;

i) an A genotype in the heterozygous or homozygous state for SNP marker 9 in SEQ ID NO: 41; and/or j) a T genotype in the heterozygous or homozygous state for SNP marker 10 in SEQ ID NO: 46.

thereby identifying a melon plant exhibiting resistance to FOM 1,2.

In a further embodiment, the invention relates to the method of the preceding embodiment, wherein said method further comprises selecting a melon plant comprising said one or more SNP markers, and crossing the selected melon plant with a second melon plant to produce progeny melon plants that comprise at least one of said SNP markers and exhibits resistance to FOM 1,2.

In another embodiment the invention relates to a method of identifying a melon plant comprising the FOM 1,2 resistance-conferring introgressed sequence of the invention, wherein said method comprises the steps of:

a) providing a population segregating for the FOM 1,2 resistance trait, b) screening the segregating population for a member exhibiting resistance to FOM 1,2, wherein said trait can be identified by the presence of FOM 1,2 resistance-conferring introgressed sequence of the invention, c) selecting one member of the segregating population, wherein said member comprises the FOM 1,2 resistance trait.

In a further embodiment, the invention provides a method for identifying a cultivated melon plant comprising an introgressed sequence on chromosome 4, wherein said introgressed sequence confers resistance to FOM 1,2, comprising:

a) providing a population segregating for FOM 1,2 resistance, b) screening said population using a kit which detects at least one of the SNP markers listed in Table 5, and, c) identifying a plant comprising said at least one SNP marker selected in the list of Table 5.

In a further embodiment, the invention provides a method for identifying a wild melon source of FOM 1,2 resistance trait on chromosome 4, comprising:

a) providing a wild melon accession or a plurality of wild melon accessions, b) screening said melon accession or plurality of wild melon accessions using a kit which detects at least one of the SNP markers listed in Table 5, and, c) identifying a wild melon accession comprising said at least one SNP marker selected in the list of Table 5.

In yet another embodiment, the invention relates to the use a SNP marker amplified from the genome of a melon plant according to any of the preceding embodiments, preferably from the genome of melon line 19MFR011167, representative seed of which is deposited under NCIMB Accession No. 43448, or a progeny or an ancestor thereof, wherein said SNP marker is identified using one of the following kits:

a) forward primer of SEQ ID NO: 2 and reverse primer of SEQ ID NO: 5, and probe of SEQ ID NO: 3;

b) forward primer of SEQ ID NO: 7 and reverse primer of SEQ ID NO: 10, and probe of SEQ ID NO: 8;

c) forward primer of SEQ ID NO: 12 and reverse primer of SEQ ID NO: 15, and probe of SEQ ID NO: 13;

d) forward primer of SEQ ID NO: 17 and reverse primer of SEQ ID NO: 20, and probe of SEQ ID NO: 18;

e) forward primer of SEQ ID NO: 22 and reverse primer of SEQ ID NO: 25, and probe of SEQ ID NO: 23;

f) forward primer of SEQ ID NO: 27 and reverse primer of SEQ ID NO: 30, and probe of SEQ ID NO: 28;

g) forward primer of SEQ ID NO: 32 and reverse primer of SEQ ID NO: 35, and probe of SEQ ID NO: 33;

h) forward primer of SEQ ID NO: 37 and reverse primer of SEQ ID NO: 40, and probe of SEQ ID NO: 38;

i) forward primer of SEQ ID NO: 42 and reverse primer of SEQ ID NO: 45, and probe of SEQ ID NO: 43; and/or j) forward primer of SEQ ID NO: 47 and reverse primer of SEQ ID NO: 50, and probe of SEQ ID NO: 48;

and wherein said SNP marker is indicative of the presence of the FOM 1,2 resistance trait in a melon plant, to identify a melon plant that comprises and exhibits the FOM 1,2 resistance trait.

In a further embodiment, the invention relates to a method for assessing the genotype of a cultivated melon plant, preferably a cultivated *Cucumis melo* plant, exhibiting resistance to FOM 1,2, said method comprising the steps of:

a) providing a sample from said plant, and, b) detecting in said sample a QTL locus located on chromosome 4 and associated with said FOM 1,2 resistance, said QTL locus being flanked by SNP markers 11 and 12, and at least one of the following SNP markers:

i) a G genotype in the heterozygous or homozygous state for SNP marker 1 in SEQ ID NO: 1;

ii) an A genotype in the heterozygous or homozygous state for SNP marker 2 in SEQ ID NO: 6;

iii) an A genotype in the heterozygous or homozygous state for SNP marker 3 in SEQ ID NO: 11;

iv) a G genotype in the heterozygous or homozygous state for SNP marker 4 in SEQ ID NO: 16;

v) an A genotype in the heterozygous or homozygous state for SNP marker 5 in SEQ ID NO: 21;

vi) an A genotype in the heterozygous or homozygous state for SNP marker 6 in SEQ ID NO: 26;

vii) an A genotype in the heterozygous or homozygous state for SNP marker 7 in SEQ ID NO: 31;

viii) an A genotype in the heterozygous or homozygous state for SNP marker 8 in SEQ ID NO: 36;

ix) an A genotype in the heterozygous or homozygous state for SNP marker 9 in SEQ ID NO: 41; and/or x) a T genotype in the heterozygous or homozygous state for SNP marker 10 in SEQ ID NO: 46; and/or xi) any other DNA marker associated with said QTL locus flanked by SNP markers 11 and 12.

In a further embodiment, the invention relates to a method of identifying in a cultivated 10 melon plant, preferably a cultivated *Cucumis melo* plant, an introgressed sequence associated with an increased resistance to FOM 1,2, said method comprising the step of detecting in said plant an allele of at least one DNA marker that is genetically linked to a QTL locus associated with said increased resistance to FOM 1,2, wherein said allele maps within 10 cM, preferably within 5 cM of said QTL locus located on chromosome 4 in a genomic region flanked by SNP markers 11 and 12.

In a further embodiment, the invention relates to the method of the preceding embodiment, wherein said QTL locus can be identified by at least one of the following SNP markers a) a G genotype in the heterozygous or homozygous state for SNP marker 1 in SEQ ID NO: 1;

b) an A genotype in the heterozygous or homozygous state for SNP marker 2 in SEQ ID NO: 6;

c) an A genotype in the heterozygous or homozygous state
   for SNP marker 3 in SEQ ID NO: 11;
d) a G genotype in the heterozygous or homozygous state
   for SNP marker 4 in SEQ ID NO: 16;
e) an A genotype in the heterozygous or homozygous state
   for SNP marker 5 in SEQ ID NO: 21;
f) an A genotype in the heterozygous or homozygous state
   for SNP marker 6 in SEQ ID NO: 26;
g) an A genotype in the heterozygous or homozygous state
   for SNP marker 7 in SEQ ID NO: 31;
h) an A genotype in the heterozygous or homozygous state
   for SNP marker 8 in SEQ ID NO: 36;
i) an A genotype in the heterozygous or homozygous state
   for SNP marker 9 in SEQ ID NO: 41; and/or
j) a T genotype in the heterozygous or homozygous state
   for SNP marker 10 in SEQ ID NO: 46.

In a further embodiment, the invention relates to the method of the preceding embodiment, wherein said method further comprises the step of selecting a cultivated melon plant, preferably a cultivated *Cucumis melo* plant comprising said introgressed sequence.

In a further embodiment, the invention relates to a method of identifying a cultivated melon plant, preferably a cultivated *Cucumis melo* plant, exhibiting increased resistance to FOM 1,2 by identifying a QTL associated with said increased resistance to FOM 1,2, the method comprising the steps of:

a) detecting at least one DNA marker from a melon plant, which DNA marker is linked to a chromosomal interval associated with increased resistance to FOM 1,2, wherein said chromosomal interval is flanked on each side by SNP markers having at least 80% sequence identity to SEQ ID NOs: 51 and 56; and b) identifying said melon plant comprising said at least one DNA marker.

Uses.

The present invention also relates to the use of FOM 1,2 resistance-propagating material obtainable from a melon plant according to any of the preceding embodiments for growing a melon plant in order to produce FOM 1,2 resistant melon plants wherein said FOM 1,2 resistance may be assessed in a standard assay, particularly an assay as described in Example 2 below.

The present invention also relates to the use of FOM 1,2 resistance propagating material obtainable from a melon plant according to any of the preceding embodiments for producing melon fruits.

The present invention also contemplates the use of the FOM 1,2 resistance genetic sequence of the present invention in association with other genetic sequences associated with FOM 1,2 resistance, for instance those genetic sequences disclosed in WO2009/000736.

In another embodiment the invention relates to the use a cultivated melon plant, plant part or seed, more preferably a cultivated *Cucumis melo* plant, plant part or seed according to any of the preceding embodiments for growing a plant and producing and harvesting crops and/or fruits.

In another embodiment the invention relates to the use of a cultivated melon plant, more preferably a cultivated *Cucumis melo* plant, according to any of the preceding embodiments for producing fruits for the fresh market or for food processing.

In another embodiment the invention relates to the use of a cultivated melon plant, plant part or seed, preferably a cultivated *Cucumis melo* plant, plant part or seed according to any of preceding embodiments, wherein said cultivated melon plant, plant part or seed, preferably the cultivated

*Cucumis melo* plant, plant part or seed is of melon line 19MFRO11167, representative seed of which is deposited under NCIMB Accession No. 43448, or a progeny or an ancestor thereof.

In a further embodiment the invention relates to the use of a cultivated melon plant, plant part or seed, more preferably a cultivated *Cucumis melo* plant, plant part or seed according to any of the preceding embodiments to sow a field, a greenhouse, or a plastic house.

In a further embodiment the invention relates to the use of a melon plant according to any of the preceding embodiments to confer the increased FOM 1,2 resistance trait to a melon plant lacking said trait. The invention further relates to the use of a melon plant according to any of the preceding embodiments to introgress an increased FOM 1,2 resistance trait into a melon plant lacking said trait.

In a further embodiment the invention relates to the use of any of SEQ ID NOs 1-60 for screening a population of melon plants for the presence of a QTL locus located on chromosome 4 and associated with an increased FOM 1,2 resistance. In a further embodiment the invention relates to the use of any of SEQ ID NOs 1, 6, 11, 16, 21, 26, 31, 36, 41, 46, 51 and 56 for screening a population of melon plants for the presence of a QTL locus located on chromosome 4 and associated with an increased FOM 1,2 resistance.

Based on the description of the present invention, the skilled person who is in possession of melon line 19MFR011167, representative seed of which is deposited under NCIMB Accession No. 43448, or a progeny or an ancestor thereof, comprising said introgressed genetic sequence, as described herein, has no difficulty to transfer the said introgressed genetic sequence of the present invention to other melon plants of various types using breeding techniques well-known in the art with the support of SNP markers herein disclosed.

Seed Deposit Details

Applicant has made a deposit of 2500 seeds of *Cucumis melo* subsp. *melo* Charentais line 19MFR011167 with NCIMB (NCIMB Limited, Ferguson Building, Craibstone Estate, Bucksburn, Aberdeen AB21 9YA, Scotland) on 30 Jul. 2019 under NCIMB Accession No. 43448.

Applicant elects for the expert solution and requests that the deposited material be released only to an Expert according to Rule 32(1) EPC or corresponding laws and rules of other countries or treaties (Expert Witness clause), until the mention of the grant of the patent publishes, or from 20 years from the date of filing if the application is refused, withdrawn or deemed to be withdrawn.

EXAMPLES

Example 1: Germplasm and Population Development

A F1 population resulting from a cross between a *Cucumis melo* subsp. *agrestis* plant and an F6 Charentais line referred to herein as "06MFR006757" was self-pollinated to obtain an F2 population referred to herein as "13MFR000612". The F2 line was then backcrossed with the same F6 Charentais line to obtain single backcross (BC1) line referred to herein as "13MFR000979". From the BC1 line "13MFR000979", lines were selected for good resistance to FOM 1,2 in climatic chambers according to the phenotypic evaluation described in Example 2 below. These lines were backcrossed to produce BC2 using the same F6 Charentais line to be evaluated for good resistance. The backcross and selection process continued until BC4. From the BC3 to BC4 segregating lines, fixed lines were derived after 5 generations of selfing and evaluated for resistance to FOM 1,2 in climatic chambers (the advanced breeding lines).

In parallel, 200 F2 plants of line "13MFR000612" were self-pollinated to produce 200 F3 lines (the F3 population). All 200 F3 lines were sown for 10 plants and evaluated for the resistance to FOM 1,2 in climatic chambers according to the phenotypic evaluation described in Example 2 below. Leaf tissue from each F2 mother plant was collected and used for DNA extraction and genotyping.

Line designated as 19MFR011167 derived from the back-cross population was identified as the most preferred line selected for FOM 1,2 resistance and has been retained and deposited at NCIMB on 30 Jul. 2019 under NCIMB Accession No. 43448. Line 19MFR011167 is a *Cucumis melo* subsp. *melo* Charentais line fixed for the FOM 1,2 resistance trait, i.e. line 19MFR011167 comprises the FOM 1,2 resistance-conferring introgressed sequence from the *Cucumis melo* subsp. *agrestis* plant at the homozygous state.

Example 2: Protocols

Example 2A. Fungal Strain

A wilting isolate of *Fusarium oxysporum* f.sp. *melonis* race 1,2 (FOM 1,2) was used for the phenotypic evaluations of the different populations as well as of lines and hybrids from advanced breeding programs. The strain was maintained at −80° C. in tubs of 20% glycerol. To perform the test, a culture was preliminary made from a small piece of agar containing mycelium from −80° C. on a sterile Petri dish of medium S (Medium S contains 1 g/l Ca(NO3)2, 0.25 g/l KNO3, 0.25 g/l MgSO4, 0.125 g/l KH2PO4, 0.125 g/l K2HPO4, 0.05 g/l citric acid, 5 g/l malt, and 50 g/l sucrose). For solid medium, 25 g of agar was added per litre of medium S, and the material was autoclaved for sterility, cooled, and poured onto Petri dishes). Active cultures were obtained by placing a small plug of mycelium from medium S culture in a flask containing 400 ml of medium S and incubating on a rotary stirrer at 130 rpm for 3 days at 21° C.

Example 2B. Preparation and Inoculation of Plants

The F3 population was evaluated for resistance to FOM 1,2 after artificial inoculation, including controls. A single experiment was carried out which included 10 plants of each F3 and controls.

Seeds were sown in trays with adapted sowing substrate. Trays were grown in climatic chambers with a photoperiod of 15 h/9 h (day/night). The temperature during the day was 22° C.±2° C. with a luminosity of 10,000 lux, and during the night the temperature was 20° C.±2° C.

The inoculation was carried out after 7 days of growth. The entire trays were soaked in a solution containing 1.5× $10^6$ spores/ml of a wilting strain of FOM 1,2 (1 litre by tray). Each tray included appropriate controls. Trays were incubated in a climatic chamber with a 10 h/14 h light/dark cycle at a temperature of 18° C./20° C.±2° C. during the night and 22° C.-24° C.±2° C. during the day. During the light cycle the luminosity was 5000 lux. Trays were watered once a day with water added of AlgospeedFlo 13-21-13 (EC=1.8-2.2), the substrate must not dry and must not be too wet.

Example 2C. Scoring of FOM 1,2 Resistance

The first symptoms (i.e., wilting on cotyledons) appeared after day 7 post-inoculation. After days 7, 10, 13 and 18 post-inoculation, the evaluation of symptoms was assessed on plants using a semi-quantitative rating scale from 1 to 9 as follows:

9=no symptoms;
7=wilting of the cotyledons or the first leaf;
5=wilting of two leaves;
3=wilting of three or more leaves;
1=death of plant.

The susceptible plants showed a wilting on cotyledons after 7 days, stop growing, and died within a few days. The intermediate resistant plants showed slowed growth and symptoms appeared on new leaves. The resistant plants did not show any symptoms on leaves and grew at a normal rate.

All plants were scored on the semi-quantitative rating scale (1-9) above. The disease scores were calculated for each F3 using adjusted mean by line with individual plant scoring using the following calculation:

$$Store=((V\times9)+(W\times7)+(X\times5)+(Y\times7)+(Z\times1))/(V+W+X+Y+Z), \text{ wherein:}$$

V=number of plants with a score equal to 9;
W=number of plants with a score equal to 7;
X=number of plants with a score equal to 5;
Y=number of plants with a score equal to 3;
Z=number of plants with a score equal to 1;

The advanced breeding lines were evaluated under similar conditions as indicated for the F3 population. The trial was done using 2 replicates of 10 plants per line following a complete block design. The evaluation of symptoms was assessed on infected leaves using the same semi-quantitative rating scale (1-9).

Example 2D. Method of Identifying the QTL and Corresponding Introgressed Sequence Underlying the FOM 1,2 Increased Resistance Trait For QTL discovery, 200 F2 individuals of the "13MFR000612" population were genotyped with 160 genetic markers spanning the genome and a genetic map was calculated. The F3 population derived from self-pollination of each of these 200 F2 individuals were grown and evaluated for FOM 1,2 as described in Example 2A-C above.

The QTL detection was performed using the R/qtl package in the R statistical framework. First, the function 'calc.genoprob' was used to calculate the genotype probabilities (step 1 cM). Haley-Knott regression was performed to provide an approximation of the results of standard interval mapping. Then, the function 'stepwiseqtl' was invoked, which provides a fully automated model selection forward/backward algorithm. LOD threshold for main effect was determine by 10,000 permutations. This algorithm considers different possible interactions (e.g., epistasis).

The function 'refineqtl' was used to refine the locations of QTL in the context of a multiple QTL model (maximum likelihood estimates). The function 'fitqtl' was used to fit a defined QTL model and obtain estimates of QTL effects.

Example 3: Identification of One QTL Associated with Increased Fom 1,2 Resistance

Example 3A. Effect of the QTL Located on Chromosome 4 on Resistance to FOM 1,2 Wilting Strain One QTL was identified based on the FOM 1,2 resistance phenotypes from the "13MFR000612" population. Table 1 shows the chromosomal location, the effect of the QTL measured as LOD score, and the percentage of variation explained by the QTL on chromosome 4 for FOM 1,2 resistance.

TABLE 1

| Significant QTL associated with FOM 1,2 resistance. | | | |
|---|---|---|---|
| Chromosome | LOD | % var | Pvalue (Chi2) |
| 4 | 11.29 | 23.1 | <0.001 |

"LOD" = log likelihood score,
"% var" = percent phenotypic variation explained by the QTL,
"Pvalue (Chi2)" = the probability of the QTL detected due to random chance by chi-square analysis.

The QTL showed a semi-dominant effect in the "13MFR000612" discovery population. The presence of only one of the resistant parent alleles at the QTL location is increasing the disease resistance score from a susceptible score of <4 to a resistant score of >6 and highest resistance of >7 is observed when the QTL on chromosome 4 is homozygous for the resistant parent allele.

Example 4: Introgression of the Fom 1,2 Resistance Conferring Sequence(s) into Commercial Background The *Cucumis melo* subsp. *melo* Charentais plant has orange flesh and is climacteric at maturity whereas *Cucumis melo* subsp. *agrestis* melon plants have white flesh and a very small size typical from the *agrestis* group. The genetic sequence associated with increased resistance to FOM 1,2 wilting strain present in *Cucumis melo* subsp. *agrestis* melon plants was introgressed into Charentais breeding material by selecting resistant plants after artificial test described in Example 2 and backcrossing them to Charentais breeding lines as described in Example 1.

The advanced breeding lines highlighted a similar phenotype to that of the recurrent parent in terms of orange flesh and climacteric characteristics while comprising the favourable introgressed sequence for FOM 1,2 tolerance. The phenotyping results, along with the results of testing for the presence or absence of representative markers in QTL4, are summarized in Table 2 below.

TABLE 2

| Presence or absence of flanking and characterizing SNP markers for QTL4 and corresponding FOM 1,2 phenotypes. | | | | |
|---|---|---|---|---|
| | Line | QTL4 Markers | | |
| MATID | test | 33.8 | 42 | 53.3 |
| 1. *Cucumis melo* subsp. *agrestis* parent | 8.0 | 1 | 1 | 1 |
| 2. Recurrent parent (RP) | 1.1 | 0 | 0 | 0 |
| 3. RP × *Cucumis melo* subsp. *agrestis* (F1) | 9.0 | H | H | H |

TABLE 2-continued

| Presence or absence of flanking and characterizing SNP markers for QTL4 and corresponding FOM 1,2 phenotypes. | | | | |
|---|---|---|---|---|
| | Line | QTL4 Markers | | |
| MATID | test | 33.8 | 42 | 53.3 |
| 4. 16MFR008784 | 9.0 | 1 | 1 | 0 |
| 5. 18MFR006635 | 7.2 | 1 | 1 | 1 |
| 6. 18MFR006650 | 8.5 | 1 | 1 | 1 |
| 7. 18MFR006694 | 9.0 | 1 | 1 | 1 |
| 8. 18MFR006902 | 7.6 | 0 | 1 | 1 |
| 9. 18MFR006903 | 8.1 | 1 | 1 | 1 |
| 10. 18MFR006908 | 8.3 | 1 | 1 | 1 |
| 11. 18MFR006912 | 8.6 | 1 | 1 | 1 |
| 12. 18MFR006923 | 8.9 | 0 | 1 | 1 |
| 13. 18MFR006924 | 8.4 | 1 | 1 | 1 |
| 14. 18MFR006956 | 8.8 | 1 | 1 | 1 |
| 15. 18MFR006958 | 8.0 | 1 | 1 | 1 |
| 16. 18MFR006959 | 8.9 | 1 | 1 | 1 |
| 17. 18MFR006894 | 2.4 | 1 | 0 | 0 |
| 18. 18MFR006916 | 1.2 | 0 | 0 | 1 |
| 19. 13MFR000699 (LM rupia FRQ9) | 5.8 | 0 | 0 | 0 |
| 20. MANTA | 2.4 | 0 | 0 | 0 |
| 21. LUNASOL | 2.1 | 0 | 0 | 0 |
| 22. FORTAL | 2.0 | 0 | 0 | 0 |

Existing commercial hybrids (MANTA, LUNASOL, FORTAL) as well as the recurrent Charentais parent are susceptible to the FOM 1,2 wilting strain. On the contrary, all advanced breeding lines comprising the QTL4 (lines 4 to 16) exhibit increased FOM 1,2 resistance with a disease score > to 7. The level of FOM 1,2 resistance in these advanced backcross breeding lines is also higher than materials comprising the QTL located on chromosome 9 as disclosed in WO2009/000736 (line 19, disease score of 5.8).

Example 5: Fine-Mapping of QTL4 Introgression

In order to reduce the QTL4 interval, variants with different allelic states between the *Cucumis melo* subsp. *agrestis* resistant parent and 06MFR006757 susceptible recurrent parent, covering the confidence interval of QTL4, were selected and converted into Taqman™ PCR assays to detect SNPs. These markers were used to genotype a large F2 population of 1068 individuals derived from the cross between an advanced breeding line exhibiting high level of resistance (18MFR006913) and the recurrent F6 Charentais line 06MFR006757. Recombinant F2 individuals were selected and self-pollinated following single seed descent breeding schema using marker assisted selection to fix selected marker haplotypes and recombination events within the QTL4 interval. A total of 23 F4 lines with distinct marker haplotypes including recombinants were produced and evaluated for FOM 1,2 resistance. The phenotyping results, along with the results of testing for the presence or absence of representative markers in QTL4 are summarized in Table 3 below.

TABLE 3

| Presence or absence of flanking and characterizing SNP markers for QTL4 and corresponding FOM 1,2 phenotypes. | | | | | | | |
|---|---|---|---|---|---|---|---|
| | | QTL4 region | | | | | |
| MATID | Line test | 33.8 | 36.7 | 41.5 | 42.2 | 45.6 | 47.7 |
| 1. 18MFR006497 original donor | 7.9 | 1 | 1 | 1 | 1 | 1 | 1 |
| 2. Recurrent parent (RP) | 1.2 | 0 | 0 | 0 | 0 | 0 | 0 |
| 3. 18MFR006913 (converted donor) | 8.9 | 1 | 1 | 1 | 1 | 1 | 1 |

TABLE 3-continued

Presence or absence of flanking and characterizing SNP
markers for QTL4 and corresponding FOM 1,2 phenotypes.

| | | | | | QTL4 region | | |
|---|---|---|---|---|---|---|---|
| MATID | Line test | 33.8 | 36.7 | 41.5 | 42.2 | 45.6 | 47.7 |
| 4. 19MFR012648 | 1.3 | 0 | 0 | 1 | 1 | 1 | 1 |
| 5. 19MFR012649 | 1.6 | 0 | 0 | 0 | 0 | 0 | 0 |
| 6. 19MFR012650 | 9 | 1 | 1 | 1 | 0 | 0 | 0 |
| 7. 19MFR012652 | 2.4 | 1 | 0 | 0 | 0 | 0 | 0 |
| 8. 19MFR012653 | 9 | 1 | 1 | 1 | 1 | 1 | 1 |
| 9. 19MFR012655 | 9 | 1 | 1 | 1 | 1 | 0 | 0 |
| 10. 19MFR012658 | 9 | 1 | 1 | 1 | 1 | 1 | 1 |
| 11. 19MFR012659 | 9 | 0 | 1 | 1 | 1 | 1 | 1 |
| 12. 19MFR012664 | 2.3 | 0 | 0 | 0 | 0 | 0 | 0 |
| 13. 19MFR012667 | 1.1 | 0 | 0 | 0 | 0 | 1 | 1 |
| 14. 19MFR012669 | 1 | 1 | 1 | 0 | 0 | 0 | 0 |
| 15. 19MFR012671 | 1.5 | 0 | 0 | 0 | 1 | 1 | 1 |
| 16. 19MFR012675 | 1 | 0 | 0 | 0 | 0 | 0 | 1 |
| 17. 19MFR012681 | 9 | 1 | 1 | 1 | 1 | 1 | 0 |
| 18. 19MFR012683 | 1.9 | 0 | 0 | 0 | 1 | 1 | 1 |
| 19. 19MFR012690 | 9 | 1 | 1 | 1 | 1 | 0 | 0 |
| 20. 19MFR012692 | 8.9 | 1 | 1 | 1 | 1 | 1 | 0 |
| 21. 19MFR012694 | 2.7 | 1 | 0 | 0 | 0 | 0 | 0 |
| 22. 19MFR012699 | 1.3 | 0 | 0 | 0 | 0 | 1 | 1 |
| 23. 19MFR012700 | 9 | 0 | 1 | 1 | 1 | 1 | 1 |
| 24. 19MFR012702 | 1.8 | 0 | 0 | 0 | 0 | 0 | 1 |
| 25. 19MFR012714 | 1.7 | 1 | 1 | 0 | 0 | 0 | 0 |
| 26. 19MFR012717 | 1 | 0 | 0 | 1 | 1 | 1 | 1 |
| 27. MFR0001225 - MANTA | 2.1 | 0 | 0 | 0 | 0 | 0 | 0 |
| 28. 13MFR000699 (LM rupia FRQ9) | 3.9 | 0 | 0 | 0 | 0 | 0 | 0 |

All lines (e.g. line 6) comprising the SNP markers spanning genetic interval 36.7-41.5 cM and therefore comprising the introgressed sequence underlying QTL4 (as fine-mapped in this Example) exhibit increased FOM 1,2 resistance with a disease score > to 8.5. The effect of the presence of the QTL4 in this trial were further observed phenotypically. The recurrent and susceptible Charentais line placed on each border (positions 1 and 12 of the tray) started to express symptoms of wilting 13 days after inoculation and die completely after 18 days whereas the converted lines (19MFR012700 and 18MFR006913 on positions 5 and 11 of the tray) did not express symptoms even after 22 days post-inoculation (FIG. 1).

Within this region, ten SNPs, SE3851, SE3886, SE3870, SE3929, SE3882, SE3864, SE3927, SE3883, SE3874 and SE3863 within the QTL interval showed specificity for the selection of donor resistant allele, and from them, SNP markers SE3864, SE3927, SE3883 and SE3874, were the most closely linked to the resistance. Table 4 shows both genetic and physical positions of the QTL4 on chromosome 4 as well as the positions of the ten SNP markers tightly linked with the QTL.

TABLE 4

Genetic map of the QTL on chromosome 4

| SNP ID | SNP Locus | Position (cM) | Physical position PIT92 v7 (bp) | Physical position Public v CM3.6.1 (bp) | Observation |
|---|---|---|---|---|---|
| 11 | SE2843 | 36.7 | 3620560 | 30695800 | Right flanking marker |
| 1 | SE3851 | 36.8 | 3640452 | 30675821 | SNP specific to R allele |
| 2 | SE3886 | 37.8 | 3735138 | 30581208 | SNP specific to R allele |
| 3 | SE3870 | 38.3 | 3767221 | 30549138 | SNP specific to R allele |
| 4 | SE3929 | 38.7 | 3799206 | 30517190 | SNP specific to R allele |
| 5 | SE3882 | 38.8 | 3829324 | 30487098 | SNP specific to R allele |
| 6 | SE3864 | 39 | 3889458 | 30426998 | SNP specific to R allele |
| 7 | SE3927 | 39.1 | 3923839 | 30392634 | SNP specific to R allele |
| 8 | SE3883 | 39.5 | 3956453 | 30365842 | SNP specific to R allele |
| 9 | SE3874 | 40 | 3985443 | 30331050 | SNP specific to R allele |
| 10 | SE3863 | 40.3 | 4018040 | 30298473 | SNP specific to R allele |
| 12 | SE3587 | 41.5 | 4088428 | 30228111 | Left flanking marker |

Example 6: Sequence and SNP Marker Information
for QTL4

The sequence information of SNP markers SE3851, SE3886, SE3870, SE3929, SE3882, SE3864, SE3927, SE3883, SE3874 and SE3863, and their respective PGR primers/probes for detection is summarized in Table 5 below.

TABLE 5

| | MARKER | | | | | | | | | | | |
|---|---|---|---|---|---|---|---|---|---|---|---|---|
| | 1/ SE3851 | 2/ SE3886 | 3/ SE3870 | 4/ SE3929 | 5/ SE3882 | 6/ SE3864 | 7/ SE3927 | 8/ SE3883 | 9/ SE3874 | 10/ SE3863 | 11/ SE2843 | 12/ SE3587 |
| Resistance (*agrestis*) Allele | G | A | A | G | A | A | A | A | A | T | G | A |
| Susceptible (*melo*) Allele | A | G | G | A | T | G | G | G | G | A | A | C |
| Target Sequence: SEQ ID NO. | 1 | 6 | 11 | 16 | 21 | 26 | 31 | 36 | 41 | 46 | 51 | 56 |
| SNP Position in Target SEQ: nt | 95 | 113 | 73 | 239 | 163 | 59 | 119 | 69 | 136 | 108 | 104 | 81 |
| Forward Primer: SEQ ID NO. | 2 | 7 | 12 | 17 | 22 | 27 | 32 | 37 | 42 | 47 | 52 | 57 |
| Reverse Primer: SEQ ID NO. | 5 | 10 | 15 | 20 | 25 | 30 | 35 | 40 | 45 | 50 | 55 | 60 |
| Probe (Resistant): SEQ ID NO. | 3 | 8 | 13 | 18 | 23 | 28 | 33 | 38 | 43 | 48 | 53 | 58 |
| Probe (Susceptible): SEQ ID NO. | 4 | 9 | 14 | 19 | 24 | 29 | 34 | 39 | 44 | 49 | 54 | 59 |

As a matter of example, SNP marker 1 (SE3851) at position 3640452 bp/30675821 bp on chromosome 4 (based on reference PIT92 v7 sequence or public genome version CM3.6.1 respectively) is characterized by a particular SNP marker (resistant vs. susceptible allele) at position 95 of the target sequence of SEQ ID NO:1. Corresponding forward and reverse primers of SEQ ID NOs 2 and 5, and probes specific for the resistant or susceptible alleles of SEQ ID NOs 3 and 4 are also disclosed.

BIBLIOGRAPHY

Herman and Perl-Treves, (2007), Plant Dis. 91(9):1180-1186.
Oumouloud et al. (2013), Euphytica 192(2):155-169.
Perchepied et al. (2005), Theoretical and Applied Genetics 111(1):65-74.
Risser et al., (1976), Phytopathology 66:1105-1106.
Zink and Gubler, (1985), J. Am. Soc. Hortic. Sci. 110:600.

The invention claimed is:

1. A cultivated melon plant, which is a cultivated *Cucumis melo* plant, resistant to *Fusarium oxysporum* f.sp. *melonis* race 1,2 (FOM 1,2) infection, comprising in its genome an introgressed sequence from *C. melo* subsp. *agrestis* which confers resistance to FOM 1,2, wherein said introgressed sequence is comprised in melon line 19MFR011167, representative seed of which is deposited under NCIMB Accession No. 43448, or a progeny thereof, is located on chromosome 4 and comprises at least one of the following SNP markers:

a) a G genotype in the heterozygous or homozygous state for SNP marker 1 at a position corresponding to position 95 in SEQ ID NO: 1;

b) an A genotype in the heterozygous or homozygous state for SNP marker 2 at a position corresponding to position 113 in SEQ ID NO: 6;

c) an A genotype in the heterozygous or homozygous state for SNP marker 3 at a position corresponding to position 73 in SEQ ID NO: 11;

d) a G genotype in the heterozygous or homozygous state for SNP marker 4 at a position corresponding to position 239 in SEQ ID NO: 16;

e) an A genotype in the heterozygous or homozygous state for SNP marker 5 at a position corresponding to position 163 in SEQ ID NO: 21;

f) an A genotype in the heterozygous or homozygous state for SNP marker 6 at a position corresponding to position 59 in SEQ ID NO: 26;

g) an A genotype in the heterozygous or homozygous state for SNP marker 7 at a position corresponding to position 119 in SEQ ID NO: 31;

h) an A genotype in the heterozygous or homozygous state for SNP marker 8 at a position corresponding to position 69 in SEQ ID NO: 36;

i) an A genotype in the heterozygous or homozygous state for SNP marker 9 at a position corresponding to position 136 in SEQ ID NO: 41; and/or j) a T genotype in the heterozygous or homozygous state for SNP marker 10 at a position corresponding to position 108 in SEQ ID NO: 46.

2. The plant according to claim 1, wherein:

a) the G genotype for SNP marker 1 can be identified in a PCR by amplification of a nucleic acid fragment with a pair of oligonucleotide primers: forward primer of SEQ ID NO: 2 and reverse primer of SEQ ID NO: 5, and probe of SEQ ID NO: 3;

b) the A genotype for SNP marker 2 can be identified in a PCR by amplification of a nucleic acid fragment with a pair of oligonucleotide primers: forward primer of SEQ ID NO: 7 and reverse primer of SEQ ID NO: 10, and probe of SEQ ID NO: 8;

c) the A genotype for SNP marker 3 can be identified in a PCR by amplification of a nucleic acid fragment with a pair of oligonucleotide primers: forward primer of SEQ ID NO: 12 and reverse primer of SEQ ID NO: 15, and probe of SEQ ID NO: 13;

d) the G genotype for SNP marker 4 can be identified in a PCR by amplification of a nucleic acid fragment with a pair of oligonucleotide primers: forward primer of SEQ ID NO: 17 and reverse primer of SEQ ID NO: 20, and probe of SEQ ID NO: 18;

e) the A genotype for SNP marker 5 can be identified in a PCR by amplification of a nucleic acid fragment with a pair of oligonucleotide primers: forward primer of SEQ ID NO: 22 and reverse primer of SEQ ID NO: 25, and probe of SEQ ID NO: 23;

f) the A genotype for SNP marker 6 can be identified in a PCR by amplification of a nucleic acid fragment with a pair of oligonucleotide primers: forward primer of SEQ ID NO: 27 and reverse primer of SEQ ID NO: 30, and probe of SEQ ID NO: 28;

g) the A genotype for SNP marker 7 can be identified in a PCR by amplification of a nucleic acid fragment with a pair of oligonucleotide primers: forward primer of SEQ ID NO: 32 and reverse primer of SEQ ID NO: 35, and probe of SEQ ID NO: 33;

h) the A genotype for SNP marker 8 can be identified in a PCR by amplification of a nucleic acid fragment with a pair of oligonucleotide primers: forward primer of SEQ ID NO: 37 and reverse primer of SEQ ID NO: 40, and probe of SEQ ID NO: 38;

i) the A genotype for SNP marker 9 can be identified in a PCR by amplification of a nucleic acid fragment with a pair of oligonucleotide primers: forward primer of SEQ ID NO: 42 and reverse primer of SEQ ID NO: 45, and probe of SEQ ID NO: 43; and/or j) the T genotype for SNP marker 10 can be identified in a PCR by amplification of a nucleic acid fragment with a pair of oligonucleotide primers: forward primer of SEQ ID NO: 47 and reverse primer of SEQ ID NO: 50, and probe of SEQ ID NO: 48.

3. The plant according to claim 1, wherein said introgressed sequence comprises at least one of SEQ ID NO: 1, SEQ ID NO: 6, SEQ ID NO: 11, SEQ ID NO: 16, SEQ ID NO: 21, SEQ ID NO: 26, SEQ ID NO: 31, SEQ ID NO: 36, SEQ ID NO: 41 and/or SEQ ID NO: 46, or a sequence that is at least 80% identical to one or more of said sequences.

4. The plant according to claim 1, wherein said plant is heterozygous for said at least one SNP marker.

5. The plant according to claim 1, wherein said plant is homozygous for said at least one SNP marker.

6. The plant of claim 1, wherein said FOM 1,2 resistance-conferring introgressed sequence confer resistance upon FOM 1,2 wilting strains.

7. The plant of claim 1, wherein said plant is obtained by crossing melon line 19MFR011167, representative seed of which is deposited under NCIMB Accession No. 43448, or a progeny or an ancestor thereof, with a melon plant that does not contain said FOM 1,2 resistance-conferring intro-gressed sequence.

8. The plant of claim 1, wherein said plant is an inbred, a dihaploid or a hybrid plant.

9. A plant of melon line 19MFR011167, representative seed of which is deposited under NCIMB Accession No. 43448.

10. A plant part of a plant according to claim 1.

11. A seed that produces a plant or a plant part according to claim 1.

12. A method for producing a cultivated melon plant exhibiting resistance to FOM 1,2 comprising the steps of a) crossing a plant according to claim 1 with a cultivated melon plant lacking said FOM 1,2 resistance-confer-ring introgressed sequence;

b) selecting a progeny plant comprising said introgressed sequence located on chromosome 4 conferring resis-tance to FOM 1,2, said selecting step comprising detecting at least one of the following SNP markers:

i) a G genotype in the heterozygous or homozygous state for SNP marker 1 at a position corresponding to position 95 in SEQ ID NO: 1;

ii) an A genotype in the heterozygous or homozygous state for SNP marker 2 at a position corresponding to position 113 in SEQ ID NO: 6;

iii) an A genotype in the heterozygous or homozygous state for SNP marker 3 at a position corresponding to position 73 in SEQ ID NO: 11;

iv) a G genotype in the heterozygous or homozygous state for SNP marker 4 at a position corresponding to position 239 in SEQ ID NO: 16;

v) an A genotype in the heterozygous or homozygous state for SNP marker 5 at a position corresponding to position 163 in SEQ ID NO: 21;

vi) an A genotype in the heterozygous or homozygous state for SNP marker 6 at a position corresponding to position 59 in SEQ ID NO: 26;

vii) an A genotype in the heterozygous or homozygous state for SNP marker 7 at a position corresponding to position 119 in SEQ ID NO: 31;

viii) an A genotype in the heterozygous or homozygous state for SNP marker 8 at a position corresponding to position 69 in SEQ ID NO: 36;

ix) an A genotype in the heterozygous or homozygous state for SNP marker 9 at a position corresponding to position 136 in SEQ ID NO: 41; and/or x) a T genotype in the heterozygous or homozygous state for SNP marker 10 at a position corresponding to position 108 in SEQ ID NO: 46;

thereby producing a plant with enhanced resistance to FOM 1,2.

13. The method according to claim 12, wherein the method further comprises:

a) selfing the selected progeny or crossing the selected progeny with another melon plant to produce further progeny.

14. The method according to claim 13, wherein further progeny are selected and selfed/crossed for 2 to 10 more generations.

15. The method according to claim 12, wherein the plant of step a) is melon line 19MFR011167, representative seed of which is deposited under NCIMB Accession No. 43448, or a progeny or an ancestor thereof.

16. A method for producing a F1 melon plant exhibiting resistance to FOM 1,2, the method comprising crossing an inbred melon plant, which is a plant according to claim 1, with a different inbred melon plant to produce F1 hybrid progeny.

17. A method of producing melon seed, the method comprising growing a melon plant from the seed of claim 11, and allowing the plant to produce further melon seed.

18. The cultivated melon plant of claim 1, wherein the cultivated *Cucumis melo* subsp. *melo* plant.

19. The method of claim 1, wherein the cultivated melon plant is a cultivated *Cucumis melo* subsp. *melo* plant.

\* \* \* \* \*